United States Patent
Tan (10) Patent No.: US 8,628,521 B2
(45) Date of Patent: *Jan. 14, 2014

(54) DEVICE FOR CAUTERISING TISSUE AND USES THEREOF

(75) Inventor: Poh Choo Mona Tan, Singapore (SG)

(73) Assignee: Jabez Hope Pte Ltd., Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 13/415,573

(22) Filed: Mar. 8, 2012

(65) Prior Publication Data

US 2012/0226190 A1 Sep. 6, 2012

Related U.S. Application Data

(63) Continuation of application No. 11/718,033, filed as application No. PCT/SG2005/000369 on Oct. 25, 2005, now Pat. No. 8,147,483.

(51) Int. Cl.
*A61B 18/08* (2006.01)

(52) U.S. Cl.
USPC .............................................. 606/27; 606/41

(58) Field of Classification Search
USPC ................................................ 606/41, 27, 34
See application file for complete search history.

(56) References Cited

U.S. PATENT DOCUMENTS

| | | | | |
|---|---|---|---|---|
| 3,856,015 | A | * | 12/1974 | Iglesias ........................... 606/46 |
| 4,917,082 | A | * | 4/1990 | Grossi et al. .................... 606/46 |
| 5,085,659 | A | | 2/1992 | Rydell |
| 5,226,908 | A | | 7/1993 | Yoon |
| 5,234,429 | A | | 8/1993 | Goldhaber |
| 5,526,822 | A | | 6/1996 | Burbank et al. |
| 5,578,030 | A | | 11/1996 | Levin |
| 5,649,547 | A | | 7/1997 | Ritchart et al. |
| 5,769,086 | A | | 6/1998 | Ritchart et al. |
| 5,810,764 | A | * | 9/1998 | Eggers et al. ................... 604/23 |
| 6,106,524 | A | | 8/2000 | Eggers et al. |
| 6,306,132 | B1 | | 10/2001 | Moorman et al. |
| 6,613,046 | B1 | | 9/2003 | Jenkins et al. |
| 6,638,235 | B2 | | 10/2003 | Miller et al. |
| 2003/0093007 | A1 | | 5/2003 | Wood |
| 2003/0097079 | A1 | | 5/2003 | Garcia |
| 2003/0109802 | A1 | | 6/2003 | Laeseke et al. |
| 2004/0097920 | A1 | | 5/2004 | Desinger |
| 2005/0080411 | A1 | | 4/2005 | Ouchi |
| 2009/0105705 | A1 | | 4/2009 | Tan |

FOREIGN PATENT DOCUMENTS

| | | |
|---|---|---|
| DE | 1160573 | 1/1964 |
| JP | 2003220074 | 8/2003 |

OTHER PUBLICATIONS

International Preliminary Report on Patentability for corresponding International Application No. PCT/SG2005/000369 dated Jan. 31, 2007.
International Search Report from PCT/SG2005/000369 dated Jul. 10, 2006.
Written Opinion of the International Searching Authority from PCT/SG2005/000369 dated Jul. 10, 2006.
Australian Office Action dated Jul. 5, 2013, for corresponding Australian Patent Application No. 2012202804.

* cited by examiner

*Primary Examiner* — Michael Peffley
*Assistant Examiner* — Daniel Fowler
(74) *Attorney, Agent, or Firm* — Heslin Rothenberg Farley & Mesiti P.C.; Victor A. Cardona, Esq.

(57) ABSTRACT

A device for cauterising tissue is arranged to be mounted to a biopsy and/or sampling instrument and includes a conductive cauterising portion and means for heating the cauterising portion. The device may be mounted either permanently or releasably removable from the biopsy and/or sampling instrument.

15 Claims, 9 Drawing Sheets

DEVICE FOR CAUTERISING TISSUE AND USES THEREOF

CROSS REFERENCE TO RELATED APPLICATIONS

This application is continuation of U.S. Ser. No. 11/718,033, filed on Apr. 26, 2007, issued as U.S. Pat. No. 8,147,483 on Apr. 3, 2012, which is a 371 national stage filing of PCT International Application No. PCT/SG2005/000369, filed on 25 Oct. 2005, and published in English on 4 May 2006, as WO 2006/046931 A2, which claims priority to Singaporean Application No. 200406874-8 filed on 26 Oct. 2004, the entire disclosures of which are incorporated herein by reference.

FIELD OF THE INVENTION

The present invention relates to a device for cauterising tissue suitable to be mounted on a biopsy and/or sampling instrument.

BACKGROUND OF THE INVENTION

The sampling of a portion of a tissue is often necessary in many humans and animals, particularly in the diagnosis and treatment of patients with cancerous tumours, pre-malignant conditions and other diseases and disorders. In particular, it is used to exclude malignancy. A biopsy may be performed when a lesion, or an abnormal area within a tissue that could possibly represent cancerous changes, is detected. The biopsy is performed to determine the nature of the lesion or abnormal area.

Traditionally, biopsies have been performed using conventional, or 'open' surgery, which involves making a large incision on the skin and dissection down to the area in question and removing the lesion. Haemostasis is then achieved using diathermy, or an electrosurgical system, in direct contact with the bleeding tissue to stop further haemorrhage. With the advent of minimally invasive biopsy techniques, it is now possible to achieve tissue biopsy through small incisions in the skin, measuring 3 to 5 mm in length. A biopsy instrument is usually constructed as a needle-like instrument with a diameter of less than 5 mm or that which is equivalent to the intended size of the skin incision and is passed from the skin to the area in question under some form of image guidance. This is known as a percutaneous approach and is commonly performed using either ultrasound techniques or x-rays for guidance. A tract therefore needs to be created from the entry point on the skin to the lesion.

Sharp dissection of vascular tissue is usually involved in demarcating the tract and removing tissue. This often results in bleeding which may occasionally be uncontrolled. A technique of achieving haemostasis is therefore essential. It is evident that because of its approach, bleeding poses a challenge for image-guided minimally invasive biopsy techniques as haemostasis cannot be achieved in the traditional manner as would be possible in conventional biopsies.

There is a paucity of devices created to prevent uncontrolled bleeding in a consistent and effective manner following percutaneous minimally invasive biopsies. Depending on the type of tissue sampled, methods that have been employed include the application of physical pressure, adrenaline injection, argon laser coagulation, or the recent use biodegradable hydrogel polymers (http://www.surgery.arizona.edu/research/grants-research/biodegradable-hydrogels.htm) or fibrin glue which act as tissue sealants and form a physical bond with the cut surface of the tissue. Although some of these techniques have been proven useful in conventional surgery, the requirements for negotiating the tract from the skin to the lesion before its application precludes its accurate and effective use in the setting of minimally invasive percutaneous biopsy techniques. Based on current methods, effective haemostasis may not be achieved and continued bleeding or a large haematoma might result. This may require further treatment with conventional surgery. In such cases, the patient is subject to additional discomfort and distress and the advantage of a minimally invasive procedure is negated.

There is therefore a need in the art for a device that can achieve haemostasis soon after a biopsy and/or tissue sampling, so as to cause minimal bleeding and discomfort to the patient.

SUMMARY OF THE INVENTION

The present invention addresses the problems above, and in particular provides a new device for cauterising tissue.

According to one aspect, the present invention provides a device for cauterising tissue, the device arranged to be mounted to a biopsy and/or sampling instrument and comprising a conductive cauterising portion and means for heating the cauterising portion. The device may be hollow.

According to a further aspect, the cauterising portion of the device may be in the form of a ring or a part of a ring through which the biopsy and/or sampling instrument extends. According to another aspect, the cauterising portion may be at least a part of a conductive material, wherein the conductive material is in the form of any one of or a combination of a layer, a cylinder and/or a wire.

The device may also be in the form of a sleeve. The cauterising portion may be part of a conductive material. This conductive may be insulated by insulating material, leaving only the cauterising portion exposed.

The device of the present invention is to be mounted on a biopsy and/or sampling instrument such that the cauterising portion of the device is closer to the distal end of the instrument. Accordingly, the device may be mounted either permanently onto the biopsy and/or sampling instrument or be releasably removable from the instrument.

According to yet another aspect of the present invention, the device may comprise a telescoping assembly comprising at least two members, wherein the first member is co-operatively engaged with the second member.

According to a further embodiment, the device may be a sleeve having a C-shaped cross-section, said sleeve being sufficiently flexible to bend at least a portion of its length away from the instrument, whilst the remaining length remains mounted to said instrument. The uncompleted part of the cross-section of the sleeve forms a gap in the sleeve. According to a further embodiment, at least part of the gap is closed by a resilient member. For the purposes of the present invention, the term 'resilient' will be understood to encompass flexible and/or elastic material. The resilient member may be at least one elastic band or an interwoven elastic fabric. However, any suitable resilient member may be used for the present invention.

The device may be as thin as possible, such as within the thickness range of between 0.1 to 0.5 mm. In so doing, on insertion of the instrument, the device may have a minimal "drag", or "snow plough" effect, on the adjacent tissue and skin, and instead promote a "clean" insertion of the device.

The device may further be arranged to mask at least a part of a biopsy and/or sampling lateral opening on the biopsy and/or sampling instrument.

The means for heating the cauterising portion comprises connection means connecting the cauterising portion to a power supply for heating the cauterising portion. In particular, the means for heating may be connected to the conductive material.

In a further aspect, the present invention provides a method for cauterising tissue comprising the steps of:
- mounting a cauterising device of the present invention on a biopsy and/or sampling instrument;
- inserting the biopsy and/or sampling instrument into a tissue mass;
- obtaining a tissue sample; and
- cauterising the tissue.

In a more preferred embodiment, the method may further comprise an additional step between the steps of mounting the device on the instrument and inserting the instrument into a tissue mass, wherein the additional step comprises acting on the device to mask at least a part of a lateral opening on the instrument. The method may also comprise a step of rotating the instrument such that the cauterising portion of the device is in a predetermined angular orientation. Further, the tissue may be cauterised while removing the device from the tissue mass.

In a most preferred embodiment, the method is such that the instrument is first positioned into the tissue mass, followed by the mounting of the device, enabling acting on the device to mask at least a part of a lateral opening on the instrument. The method may also comprise a step of rotating the instrument such that the cauterising portion of the device is in a predetermined angular orientation. Further, the tissue may be cauterised while sliding the device within the tissue.

In a preferred embodiment, the method of cauterising tissue may also be carried out such that the cauterising device is mounted on the biopsy and/or sampling instrument after the instrument has been removed from the body after a biopsy and/or tissue sampling, followed by re-inserting the instrument into the tissue mass which has been sampled, and cauterising the tissue.

In another aspect of the present invention is a biopsy and/or sampling instrument for obtaining tissue samples and cauterising the remaining tissue comprising:
- means for sampling tissue;
- a lateral opening for receiving the tissue samples;
- a conductive cauterising portion; and
- means for heating the cauterising portion.

In a more preferred embodiment, the sampling means includes a cauterising portion. In a most preferred embodiment, the sampling means may include a coaxial cutter internal to the instrument which may have a connection to a power supply such that the cutter both samples ad cauterises tissue.

Another further aspect is a method of obtaining tissue samples and cauterising the remaining tissue comprising the steps of:
- introducing the biopsy and/or sampling instrument as described above into a tissue mass to be sampled;
- severing a tissue sample from the tissue mass that has entered the lateral opening;
- transporting the severed tissue sample to the proximal end of the instrument;
- depositing the severed tissue sample; and
- cauterising the tissue.

Accordingly, the types of tissue cauterised in the present invention include mammalian tissue. In particular, the invention relates to cauterising human tissue. Even more in particular, the invention relates to cauterising breast tissue.

According to another aspect, the invention provides a method of assembly of an instrument for cauterising tissue comprising the steps of: attaching a sheath to a shaft of a biopsy and/or sampling instrument and connecting a diathermy pin to the instrument to cauterise a tissue.

In a preferred embodiment, the sheath may function as either a conductive or insulating sheath.

Another aspect of the invention is a kit comprising a device for cauterising tissue according to any aspect of the present invention, and a biopsy and/or sampling instrument.

DETAILED DESCRIPTION OF THE INVENTION

It will be convenient to further describe the present invention with respect to the accompanying drawings that illustrate possible arrangements of the invention. Other arrangements of the invention are possible, and consequently the particularity of the accompanying drawings are not intended to be limiting of the present invention.

According to a first aspect, the present invention provides a device for cauterising tissue, the device arranged to be mounted to a biopsy and/or sampling instrument and comprising a conductive cauterising portion and means for heating the cauterising portion.

The biopsy and/or sampling instrument to which the device may be mounted to can be any biopsy and/or sampling instrument known in the art. For example, the instrument may be any one of the instruments as described by U.S. Pat. Nos. 5,526,822, 5,649,547, 5,769,086, 6,638,235, herein incorporated by reference.

According to a further aspect, the device is hollow. For the purposes of this invention, the term hollow refers to a body having a hole or space within, a cavity, opening or space in or within a body.

Figure 1A:
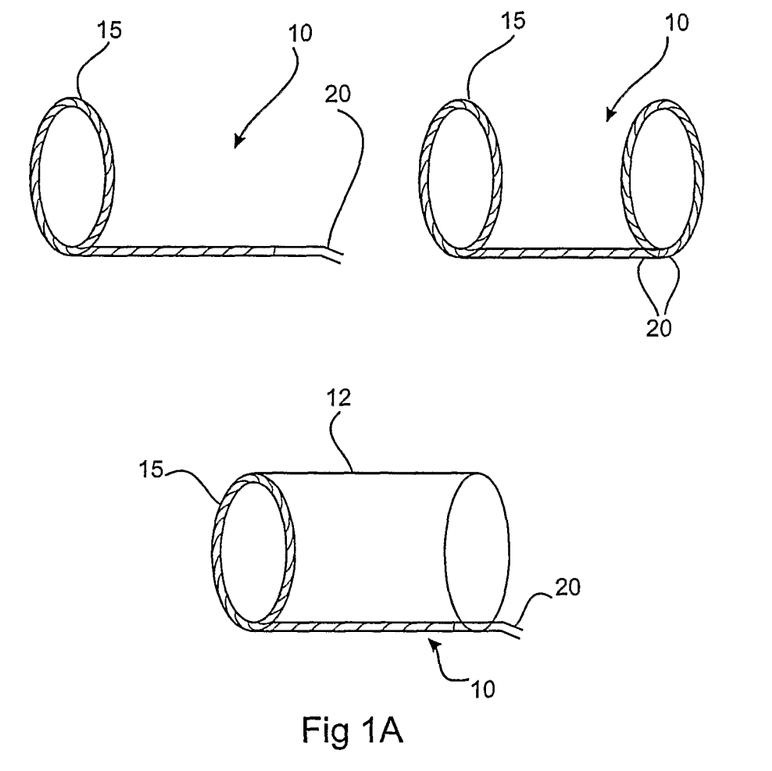
FIG. 1A is a side elevation view of the cauterising device according to one aspect of the invention.

According to FIG. 1A, it provides a cauterising device 10 comprising a conductive cauterising portion 15, and means for heating 20 the cauterising portion 15 by a power supply (not shown). The cauterising portion 15 is in the form of a ring through which a biopsy and/or sampling instrument may extend. The cauterising portion 15, however, may be a part of a ring. In this case, the remaining part of the ring, which does not act as the cauterising portion 15, is insulated by suitable insulating material. The means for heating 20 is in the form of a wire running along the length of the device 10. Alternatively, the means for heating 20 may be in the form of a ring of conductive material (as seen in FIG. 1A) attached to the cauterising portion 15 by means of a wire running along the length of the device 10. However, the means for heating 20 may be any other means by which the cauterising portion 15 may be heated or connected to a power supply.

FIG. 1A also provides an alternative arrangement of the cauterising device 10. The device 10 may be in the form of a sleeve 12 comprising a cauterising portion 15 and means for heating 20 connected to the cauterising portion 15.

Figure 1B:
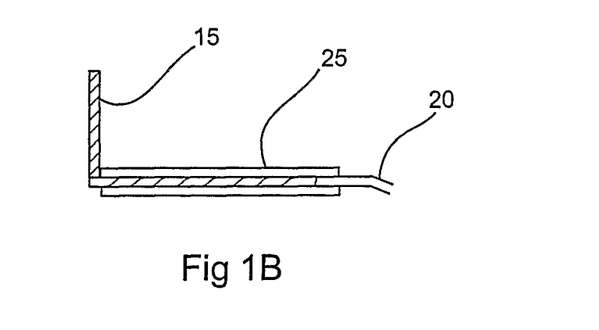
FIG. 1B is a cross sectional view of FIG. 1A.

In order to prevent the heat from being dissipated and ensuring that the heat is concentrated at the cauterising portion 15, the means for heating 20 is surrounded by an insulating material 25, as shown in FIG. 1B. For the purposes of this invention, any suitable insulating material known in the art may be used. In particular, the insulating material 25 may be a biocompatible material, as it will be inserted into a tissue mass. Examples of biocompatible materials include plastic or epoxy.

Figure 2A:
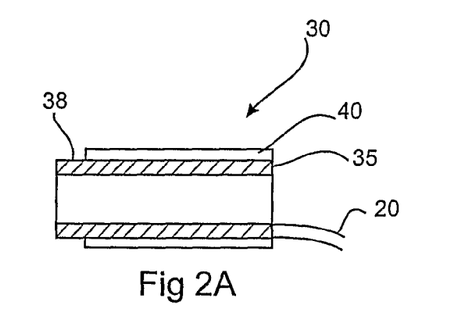
FIGS. 2A and 2B are cross sectional views of the cauterising device in the form of a sleeve.
Figure 2B:
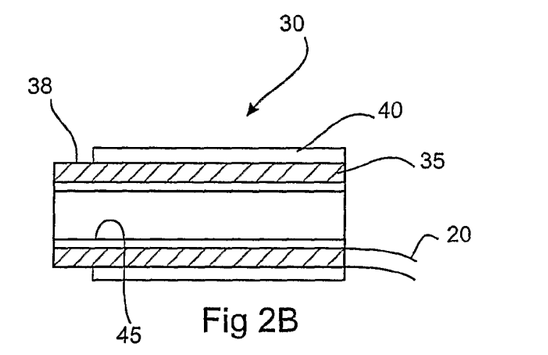

Another aspect of the present invention is shown in FIGS. 2A and 2B. FIG. 2A shows the cauterising device 30, wherein the device 30 is in the form of a sleeve. The sleeve comprises a conductive layer 35 and means for heating 20 connected to a power supply (not shown). The conductive layer 35 is further insulated by an external insulating layer 40 to prevent heat from the conductive layer 35 from being dissipated to the surrounding. Another function of the external insulating layer 40 is to prevent the patient's skin to be burnt by the heat supplied by the power supply. The external insulating layer 40 however leaves a portion of the conductive layer 35 exposed. This exposed portion of the conductive layer 35 acts as the cauterising portion 38 of the device 30, which is in the form of a ring around the sleeve. The advantage of exposing just a portion of the conductive layer 35 to act as the cauterising portion 38 is to ensure that the heat supplied is concentrated at a point and therefore the cauterising of the tissue would be more effective.

Alternatively, the conductive layer 35 may be insulated by external insulating layer 45 such that a portion of the conductive layer 35 is exposed at either ends of the device 30. The exposed portion of the conductive layer 35 at the distal end of the device acts as the cauterising portion 38, while the other exposed portion at the proximal end of the device 30 may be used as the means for heating 20, which is in turn connected to a power supply (not shown).

A further alternative of this aspect of the invention provides an inner insulating layer 45, as shown in FIG. 2B. This inner insulating layer 45 would be useful when the device 30 is mounted on a biopsy and/or sampling instrument with a shaft made of conducting material, so as to minimise heat from the conductive layer 35 from being dissipated to the shaft of the instrument.

Figure 3A:
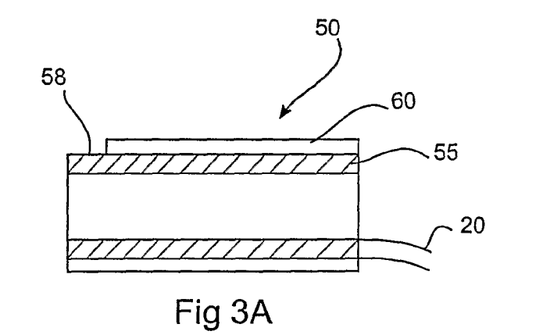
FIGS. 3A and 3B are cross sectional views of a cauterising device in the form of a sleeve according to another aspect of the invention.
Figure 3B:
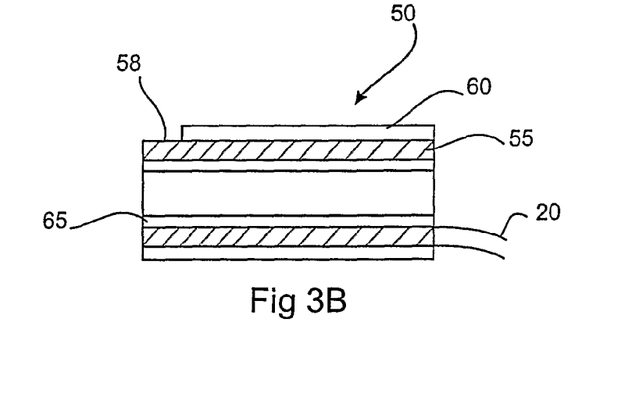

The cauterising device 50 as shown in FIGS. 3A and 3B is similar to the device of FIGS. 2A and 2B. The device 50 comprises a conductive layer 55 and an external insulating layer 60. The external insulating layer 60 leaves a portion of the conductive layer 55 exposed. This exposed portion of the conductive layer 55 forms the cauterising portion 58 of the device 50. However, in the device 50, the cauterising portion 58 forms just a part of a ring around the sleeve.

A further alternative is wherein the external insulating layer 60 leaves the conductive layer 55 exposed at either ends of the conductive layer 55. The exposed portion of the conductive layer 55 at the distal end of the device 50 acts as the cauterising portion 58, while the other exposed portion of the conductive layer 55 acts as the means for heating 20, which is in turn connected to a power supply (not shown) to heat the cauterising portion 58.

Another alternative of the present aspect is shown in FIG. 3B. The device 50 further comprises an internal insulating layer 65. This internal insulating layer 65 would be useful when device 50 is mounted on a biopsy and/or sampling instrument with a shaft made of conducting material, so as to minimise heat from being dissipated from the conductive layer 55 from being dissipated to the shaft of the instrument.

Accordingly, the conductive layer 55 may be extended at the end opposite the end with the cauterising portion 58 to permit the attachment of a diathermy pin (not shown).

Figure 4A:
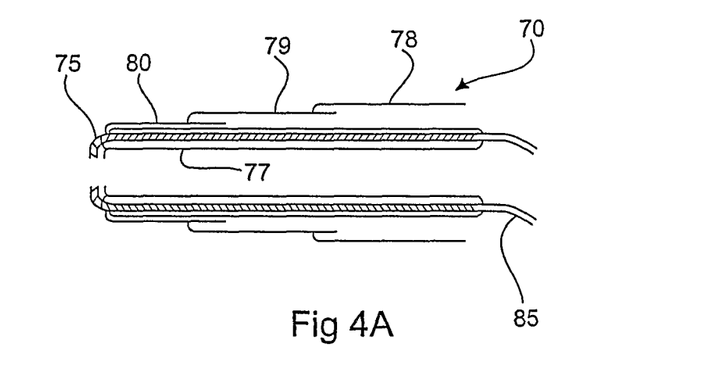
FIGS. 4A and 4B are the cross sectional views of alternative aspects of the invention, wherein the cauterising device comprises a telescopic assembly.
Figure 4B:
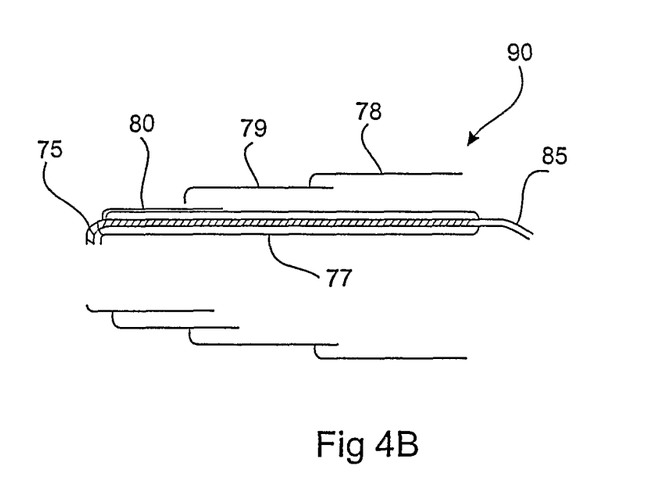

Yet another aspect of the present invention is shown in FIGS. 4A and 4B. FIGS. 4A and 4B show a cauterising device 70 and 90 respectively comprising a telescoping assembly comprising three members, 78, 79, 80, wherein the members are all co-operatively engaged with the adjacent member. In particular, member 78 is co-operatively engaged with member 79, which is in turn co-operatively engaged with member 80.

For the purposes of this invention, a telescoping assembly refers to members that fit together like a set of cylinders that slide into one another, allowing extension and shortening of the assembly. The telescoping assembly may contain any number of members, with a minimum of two members and wherein the first member is co-operatively engaged with the second member. The number of members may vary depending on the length desired to extend the device to.

Accordingly, when using the device 70 or 90, even though the telescoping assembly comprises of three members 78, 79 and 80, only member 80, comprising a cauterising portion 75, may be extended out of member 79 without the need to extend member 79 out from member 78. The members 78, 79 and 80 are made of any suitable insulating material so as to prevent the heat supplied to the cauterising portion 75 from dissipating to the surrounding. The members 78, 79 and 80 are preferably made of insulating biocompatible material. For example, plastic or epoxy.

The assembly further comprises a cauterising portion 75 which is connected to the power supply (not shown) by a wire 85. In FIG. 4A, there are two wires 85 running along the length of the assembly to connect the cauterising portion 75 to the power supply, whereas in FIG. 4B, there is only one wire 85 running along the length of the assembly to connect the cauterising portion 75 to the power supply. The wire 85 is insulated by suitable insulating material 77, leaving only the cauterising portion 75 exposed.

An alternative aspect of the invention is a telescoping assembly as described above, comprising at least two members and wherein each member comprises at least a conductive material in the form of a layer, and an external insulating layer. The member may further comprise an internal insulating layer. The conductive material of all members is arranged in such a way that the conductive material of all members of the assembly are in continuous contact. A person skilled in the art would have the relevant knowledge on how the members should be arranged such that the conductive layers of all the members are in continuous contact.

Figure 5:
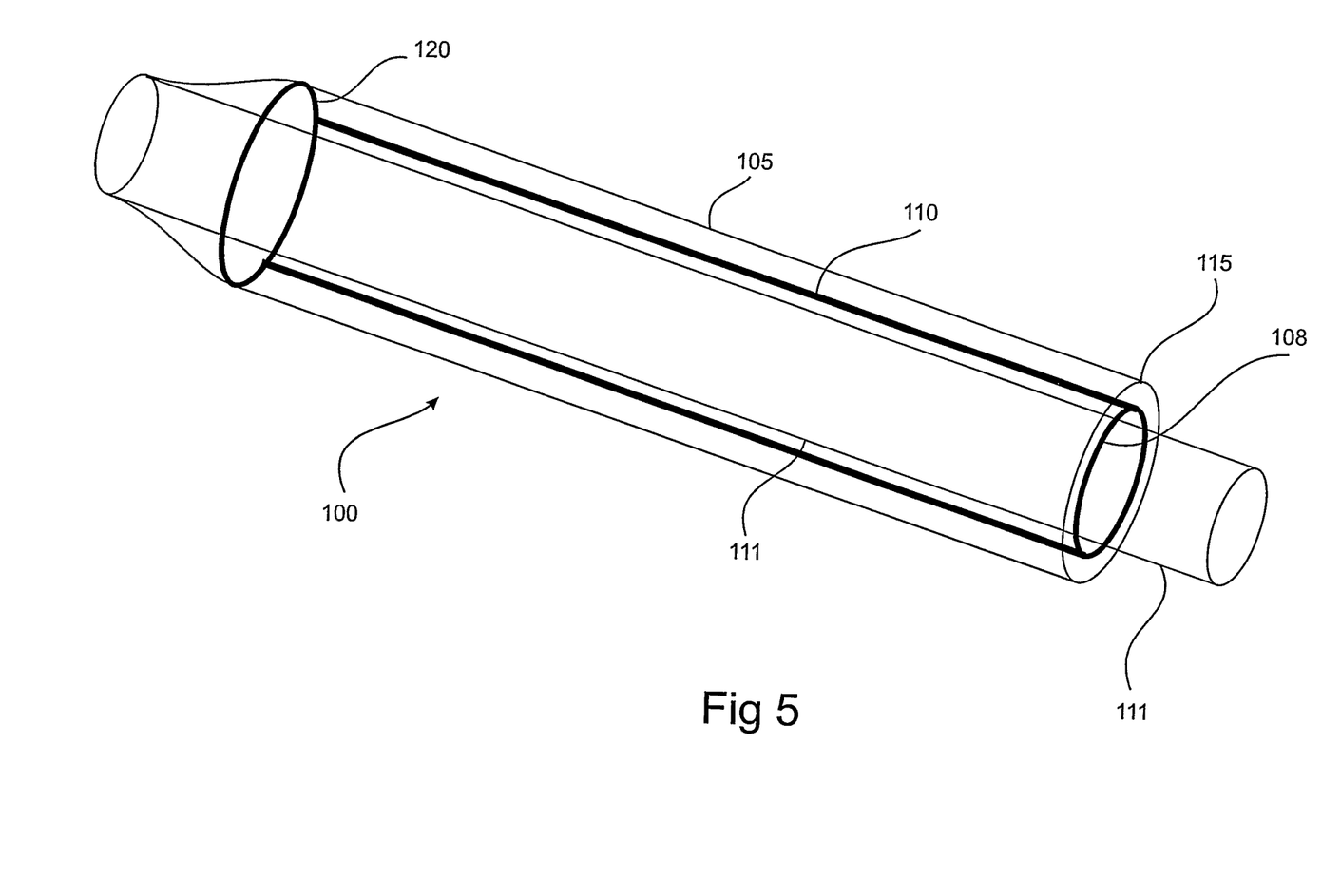
FIG. 5 shows a perspective view of a cauterising device.

According to another aspect of the present invention is the device 100 as shown in FIG. 5. The cauterising device 100 is mountable on a biopsy and/or sampling instrument. The cauterising device 100 has an orifice through which a biopsy and/or sampling instrument extends, comprising three layers: the inner layer 111 with a proximal extension, the middle conducting layer 110 with a protrusion 108 of the middle conducting layer 110 proximal to a ledge 115 and the outer layer 105. The protrusion 108 may be in the form of any one of or a combination of a layer, a cylinder and/or a wire. The device 100 further comprises a ring 120 of conductive material connected to the protrusion 108 through the middle conducting layer 110. The outer layer 105 and inner layer 111 are made of insulating material while the middle layer 110, and its protrusion 108, is made of conducting material. The three layers are such that a part of the middle conducting layer 110 is sandwiched between the inner insulating layer 111 and the outer insulating layer 105. This exposed distal part of the inner conducting layer 110 which forms the ring 120 acts as the cauterising portion when the device 100 is connected to a power supply (not shown). A possible way of connecting the device 100 to a power supply may be by attaching the power supply to conducting layer 110 either directly or through its protrusion 108. Accordingly, the device 100 is mounted on a biopsy and/or sampling instrument such that the ring 120 of the device 100 is at the distal end of the instrument, while the exposed protrusion 108 of the middle conducting layer 110 is at the proximal end of the instrument. The ledge 115, made of insulating material serves the purpose of preventing the skin from coming into contact with the conducting layer 110. The ring 120 may be a part of the middle conducting layer 110 which is not covered by the outer insulating layer 105. The middle conducting layer 110 and/or its protrusion 108, when connected to a power supply acts as the means for charging or heating ring 120, which is the cauterising portion. This middle conducting layer 110 serves as connection means between the ring 120 and the power supply to allow an electric current to charge the cauterising portion and allow heat dissipation for cautery when the ring 120 is in contact with tissue.

According to a further aspect, a diathermy pin (not shown) may be curled over the exposed protrusion 108 of the middle conducting layer 110 to be used for electric current conduction. When a user of the device 100 activates the power supply, heat is supplied to the cauterising portion, either connecting the middle conducting layer 110 or its exposed protrusion 108 directly to a power supply, or by using a diathermy pin attached (not shown) to the protrusion 108. The inner insulating layer 111 extends proximally beyond the middle conducting layer 110 creating a shelf for stable placement of such a diathermy pin.

Figure 6A:
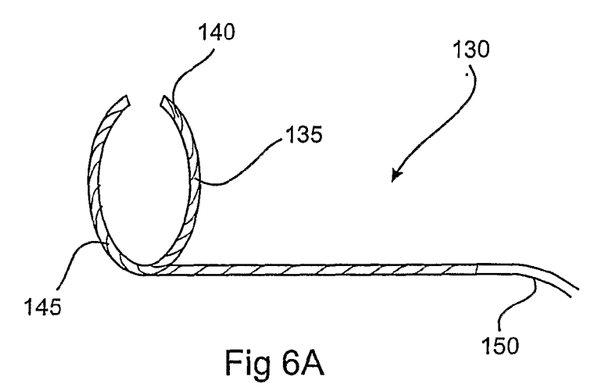
FIGS. 6A and 6B shows a side elevation and FIGS. 6C, 6D, 6E and 6F show a perspective view of an aspect of the present invention.

Another aspect of the present invention is a device 130 for cauterising tissue, as shown in FIGS. 6A$_1$ comprising a conductive cauterising portion 140 which is in the form of a part of a ring with two arms 135 and 145, through which a biopsy and/or sampling instrument extends. The device 130 may be mounted to a biopsy and/or sampling instrument according to any suitable method known in the art. The device 130 further comprises a means for heating 150, which connects the cauterising portion 140 to a power supply (not shown). The power supply heats the cauterising portion 140 when it is required to do so. Accordingly, the power supply may be controlled by the user of the device 130.

According to a further aspect, the two arms 135 and 145 may be made of flexible conductive material, such that when the device 130 is mounted to a biopsy and/or sampling instrument, the two arms 135 and 145 may be adjusted by either pressing the arms 135 and 145 closer together, in the case of a biopsy and/or sampling instrument with a smaller diameter, or pushing the arms 135 and 145 further apart, in the case of a biopsy and/or sampling instrument with a larger diameter.

Figure 6B:
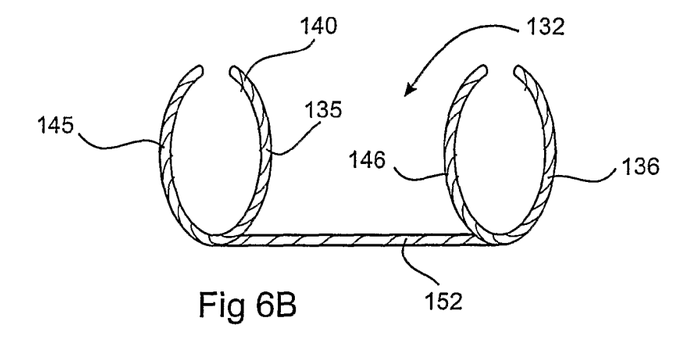

As an alternative to FIG. 6A, FIG. 6B provides a cauterising device 132, comprising a conductive cauterising portion 140 which is in the form of a part of a ring at one end of the device 132 with two arms 135 and 145, through which a biopsy and/or sampling instrument extends. The device 132 comprises another ring with two arms 136 and 146 at the other end of the device. The device 132 further comprises a means for connection 152, which connects the two rings at either ends of the device 132. The power supply needed to heat the cauterising portion 140 may be connected to either arm 146 or 136 of the device 132. The power supply heats the cauterising portion 140 when it is required to do so. Accordingly, the power supply may be controlled by the user of the device 132. Similar to the device 130 of FIG. 6A$_1$ the arms 135, 136, 145 and 146 may be made of flexible conductive material. The rings of device 130 and 132 may be split-rings.

Figure 6C:
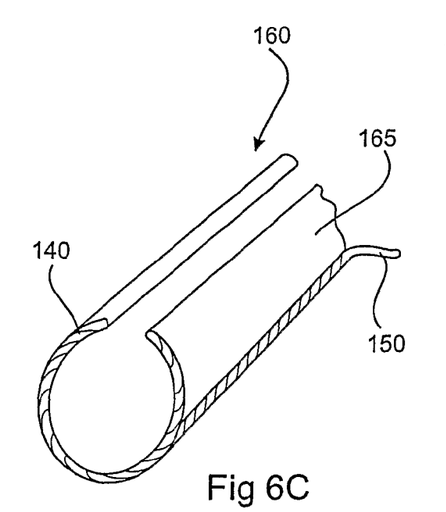

According to another further aspect, the cauterising device 160 is in the form of a hollow sleeve 165 as shown in FIG. 6C. The device 160 comprises a conductive cauterisation portion 140, which is a part of a ring through which the biopsy and/or sampling instrument extends. The sleeve 165 of the device 160 is made of flexible insulating material, while the cauterising portion is made of flexible conductive material, such that a tighter fit can be achieved when the device 160 is mounted to a biopsy and/or sampling instrument, depending on the diameter of the biopsy and/or sampling instrument. Further, there is a means for heating 150 running within the sleeve 165, through the length of the sleeve 165, which is connected to a power supply (not shown) to supply heat to the cauterising portion 140 when required.

Figure 6D:
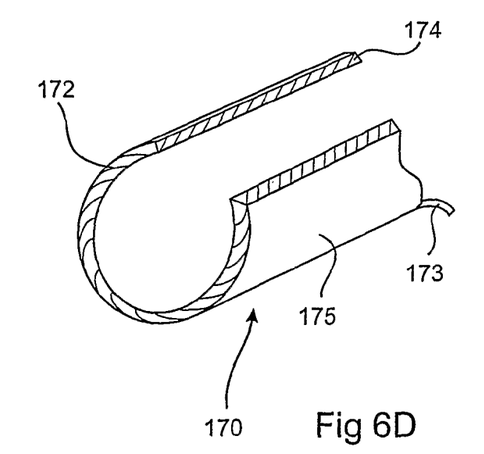

Another further aspect is shown in FIG. 6D. The device 170 works similarly to the device 160 of FIG. 6C. However, the device 170 is in the form of a hollow sleeve of conductive material 174. The device 170 comprises a cauterising portion 172. A power supply (not shown) is connected to the conductive material 174 by means of heating 173. The cauterising portion 172 is therefore heated by the power supply via the conductive material 174. The device 170 further comprises an external insulating layer 175 which covers the conductive material 174, leaving the cauterising portion 172 exposed. Similar to the device 160 of FIG. 6C, the cauterising portion 172, external insulating layer 175 and the layer of conductive material 174 is made of flexible material to achieve a better fit of the device 170 on the biopsy and/or sampling instrument when the device 170 is mounted on the instrument.

Figure 6E:
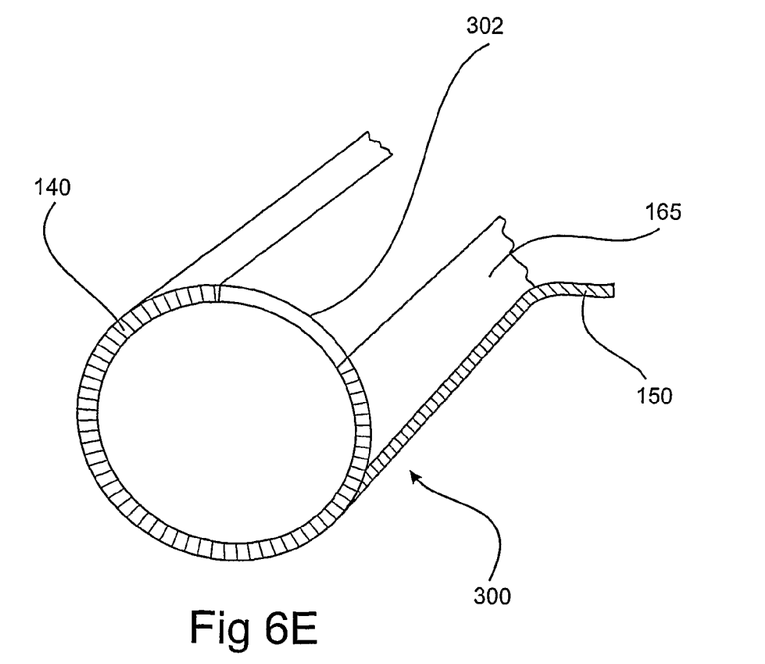

A further aspect of the present invention is shown in FIG. 6E. The device 300 of FIG. 6E works similarly to device 160 of FIG. 6C. As with device 160, the device 300 comprises a hollow sleeve 165 and a conductive cauterisation portion 140, which is part of a ring through which the biopsy and/or sampling instrument extends. The sleeve 165 of the device 300 is made of flexible insulating material, while the cauterising portion is made of flexible conductive material, such that a tight fit can be achieved when the device 300 is mounted to a biopsy and/or sampling instrument, depending on the diameter of the biopsy and/or sampling instrument. There is also a means for heating 150 running within the sleeve 165, through the length of the sleeve 165, which is connected to the power supply (not shown) to supply heat to the cauterising portion 140 when required. The device 300 further comprises an elastic band 302 to close the gap between the sleeve 165 of the device 300 at at least one part of the sleeve 165. The elastic band 302 may be attached to the cauterising portion 140 as shown in FIG. 6E. Alternatively, the elastic band 302 may be placed at any position along the length of the sleeve 165. As another alternative, there may be more than one elastic band 302 placed along the length of the sleeve 165. The elastic band 302 can be of any suitable material such that it enables the sleeve 165 to fit snugly around a biopsy and/or sampling instrument and also allow the sleeve 165 to be able to stretch beyond its original diameter without the device 300 detaching itself from the biopsy and/or sampling instrument on which it is mounted. For example, the elastic band 302 may be made of a resilient material such as rubber. However, any other suitable material may be used for the elastic band 302. The elastic band 302 may be attached to the sleeve 165 by an adhesive such as glue or the like. Alternatively, there may be means provided on the cauterising portion 140 and/or the sleeve 165 for the connection of the elastic band(s) 302.

Figure 6F:
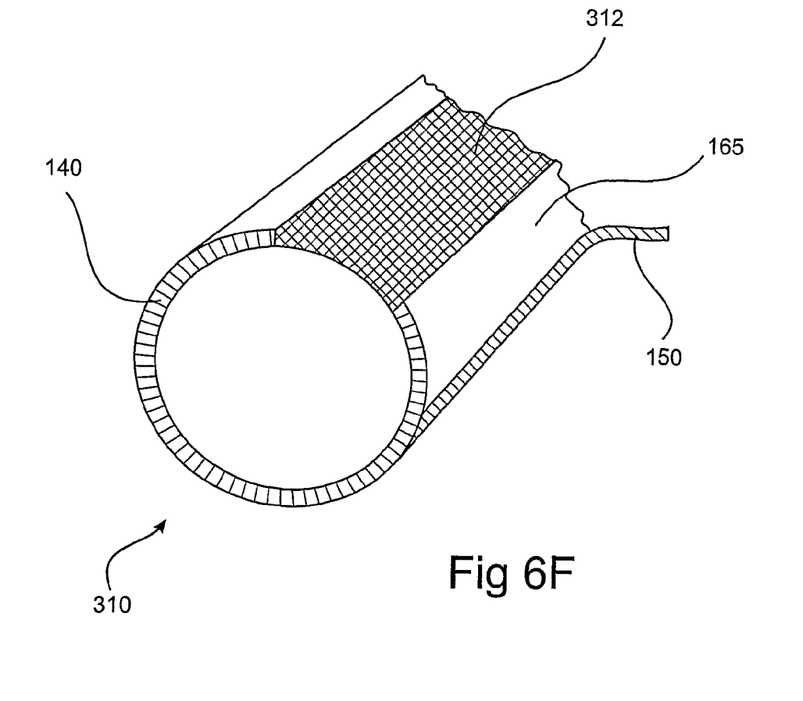

Another further aspect of the present invention is provided in FIG. 6F. The device 310, as shown in FIG. 6F, is similar to the device 300 of 6E. However, instead of the use of elastic band(s) 302, the device 310 uses a resilient material 312 to cover the gap between the sleeve 165. The resilient material 312 may be in the form of an interwoven elastic material, or any suitable elastic and/or flexible material may be used. For example, an interwoven elastic fabric may be used as the resilient material 312. The resilient material 312 can be of any suitable material such that it enables the sleeve 165 to fit snugly around a biopsy and/or sampling instrument and also allow the sleeve 165 to be able to stretch beyond its original diameter without the device 300 detaching itself from the biopsy and/or sampling instrument on which it is mounted. The resilient material 312 may be attached to the sleeve 165 by a suitable adhesive such as glue or the like. Alternatively, means may be provided on the sleeve 165 and/or the cauterising portion 140 to attach the resilient material 312 to itself.

Figure 7:
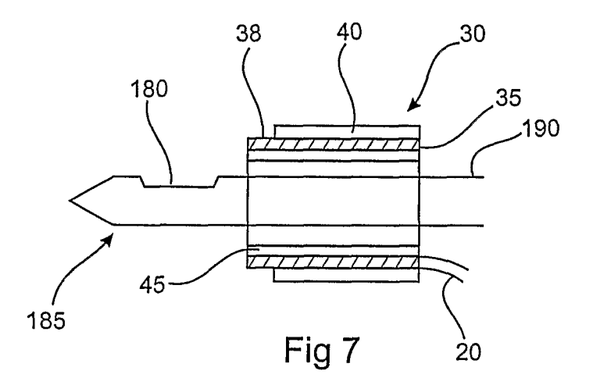
FIG. 7 illustrates how the cauterising device of the present invention may be mounted on a biopsy and/or sampling instrument.

Another aspect of the present invention is shown in FIG. 7. FIG. 7 shows how the device 30 may be used together with a biopsy and/or sampling instrument 185. However, this aspect of the invention is not limited to the device 30 but any device which is within the scope of the present invention. FIG. 7 is also not limited to the use of biopsy and/or sampling instrument 185, but any suitable biopsy and/or sampling instrument may be used according to this aspect of the invention. The device 30 is mounted to the biopsy and/or sampling instrument 185 such that the cauterising portion 38 of the device 30 is closer to the distal end of the instrument 185. According to FIG. 7, the device 30 is mounted to a shaft 190 of the instrument 185. The instrument 185 further comprises a lateral opening 180 for receiving tissue samples.

The device 30 can be mounted on instrument 185 by any suitable method. The device 30 may be mounted either permanently or releasably removable from the instrument 185. For example, the device 30 may be mounted on instrument 185 by frictional contact between the instrument 185 and the device 30. This can be done by passing the instrument 185 through the hollow device 30, and the device 30 will consequently be held in place by frictional contact. Therefore, according to this aspect, no further mounting means are required.

The device 30 is also able to slide along the shaft 190 of the instrument 185. This enables the device 30 to mask at least a part of the lateral opening 180 when such a large opening is not required for tissue sampling. For example, in a breast biopsy which uses a breast biopsy instrument such as that described in U.S. Pat. No. 5,526,822, in many patients an adequate thickness with compression of the breast may not be achieved to carry out the biopsy procedure. For example, stereotactic percutaneous vacuum-assisted breast biopsy of the breast requires the breast to be compressed before the biopsy. The vacuum biopsy device has a fixed biopsy chamber (aperture) length and a requirement for a minimum compression. As a result, there are occasions when the lesion is too close to the skin or when the compression is too narrow to accommodate the biopsy detail of the instrument. In the first instance there will be a portion of the aperture that extends beyond the skin and leaves it open to the air. Vacuum suction therefore cannot be achieved. In the second instance, biopsy is often aborted and the patient would have to subject to conventional 'open' surgery. Other examples in which only a part of the lateral opening would be required include when only the distal part of the instrument needs to be inserted into the breast, only a small tissue sample is required or if the area to be sampled is found very near to the skin. It would therefore be advantageous to be able to use the device to mask a part of the lateral opening in order to reduce the size of the lateral opening on the instrument. This can be seen in FIG. 8, which shows device 30 masking a part of the lateral opening 180 on the shaft 190 of the instrument 185.

According to a further aspect, the device 30 may also be held firmly in place on the instrument 185 by using any suitable mounting means known in the art. In particular, the mounting means comprises an O-ring at an interface between the device 30 and the instrument 185. Other mounting means comprise a locking mechanism between the device 30 and the instrument 185, wherein the mechanism comprises any one of the following or a combination thereof, but not limited to, a press-fit, interference fit or spring loaded mechanism. Yet another example of mounting means is an adhesive layer for adhering the device 30 to the instrument 185. The adhesive layer may be a layer of glue or any other suitable means of adhering two surfaces together.

Another aspect of the present invention is the use of the device according to any aspect of the present invention to cauterise tissue, wherein the method of cauterising tissue comprises the steps of:

mounting the cauterising device to a biopsy and/or sampling instrument;

inserting the biopsy and/or sampling instrument into a tissue mass;

obtaining a tissue sample; and cauterising the tissue.

Figure 8:
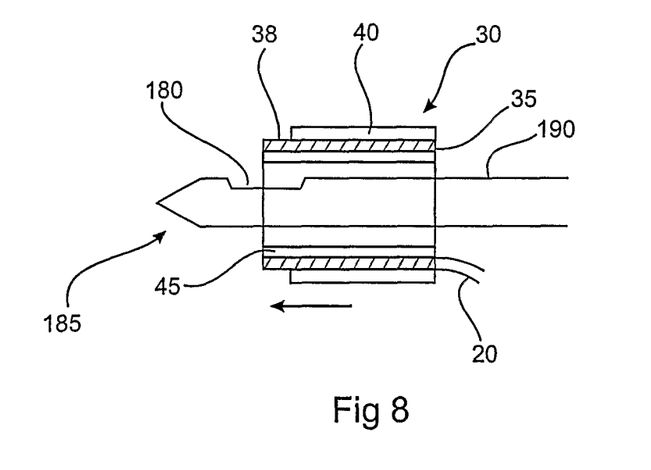
FIG. 8 shows how the cauterising device according to the present invention may be arranged to mask a part of the lateral opening of the biopsy and/or sampling instrument.

The device may be mounted to a biopsy and/or sampling instrument as shown in FIG. 7 or 8. Accordingly, the device 30 may be mounted to the instrument 185 before a tissue sample has been obtained, followed by inserting the instrument 185 with the device 30 into a tissue mass which is desired to be sampled. The tissue sample can then be obtained by any suitable method. For example, the method as described in any one of U.S. Pat. Nos. 5,526,822, 5,649,547, 5,769,086, 6,638, 235. Once the tissue sample has been obtained, the cauterising portion 38 is heated via the means for heating 20 which heats the cauterising portion 38, for example by connecting the means for heating 20 to a power supply (not shown). For example, the cauterising portion 38 may be heated by induction. However, the cauterising portion 38 is heated only when the tissue is to be cauterised. Therefore, the power supply is controlled by the user who is able to switch on the power supply only when it is required.

The method of cauterising the tissue may further comprise an additional step between the steps of mounting the cauterising device 30 to the instrument 185 and inserting the instrument 185 into a tissue mass. This additional step comprises acting on the device 30 to mask at least a part of the lateral opening 180 on the instrument 185, as shown in FIG. 8. The method may further comprise another step of rotating the instrument 185 such that the cauterising portion 38 of the device 30 is in a predetermined angular orientation. According to a further aspect, the tissue may be cauterised while removing the instrument 185 from the tissue mass.

The method is not restricted to biopsy procedures but any tissue, which has been sampled, may be cauterised. The tissue may be mammalian tissue. In particular, the tissue may be human tissue and even more in particular, the tissue may be breast tissue. The method may also be used for cauterising kidney or liver tissues.

According to another aspect of the present invention, the method of cauterising tissue comprises the steps of.
  mounting the cauterising device to a biopsy and/or sampling instrument after the instrument has been removed from the body after a biopsy and/or tissue sampling;
  inserting the biopsy and/or sampling instrument into a tissue mass which has been sampled; and
  cauterising the tissue.

The difference between the present method and that described above is that in the present method, the device 30 is mounted on the instrument 185 after the biopsy and/or tissue sampling procedure has been carried out. After the device 30 has been mounted, the instrument 185 is re-inserted into the tissue mass which has been sampled. The tissue is then cauterised to stop secure haemostasis. The cauterisation portion 38 is heated only when the user switches on the power supply and when the user wishes to carry out cauterisation of the tissue.

Another aspect of the invention is a kit comprising a device for cauterising tissue according to any one aspect of the present invention and a biopsy and/or sampling instrument.

Another aspect of the present invention is a biopsy and/or sampling instrument for obtaining tissue samples and cauterising the remaining tissue comprising:
  means for sampling tissue;
  a lateral opening for receiving the tissue samples;
  a conductive cauterising portion; and
  means for heating the cauterising portion.

Figure 9A:
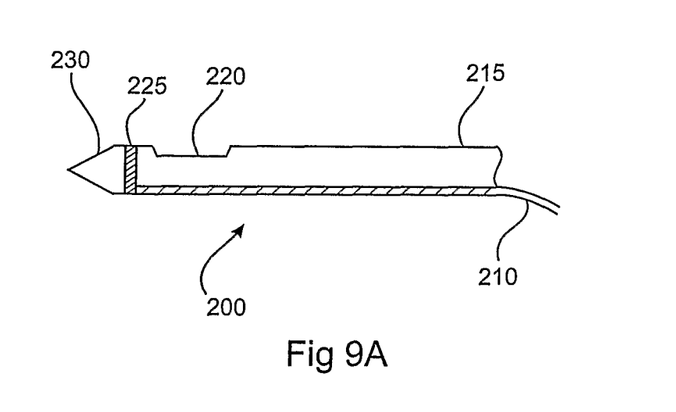
FIGS. 9A, 9B, 9C and 9D show side views of alternatives of a biopsy and/or sampling instrument with means for cauterisation present in the instrument.

An example of such an instrument is as shown in FIG. 9A. The instrument 200 comprises a pointed distal end 230, a lateral opening 220 along its hollow shaft 215, a cauterising portion 225 made of conductive material, and a wire 210 connecting the power supply to the cauterising portion 225. The instrument 200 may further comprise other features similar to instruments as described in U.S. Pat. Nos. 5,526,822, 5,649,547, 5,769,086, 6,638,235, the comments of which are incorporated herein by reference. In particular, the means of sampling include the shaft 215 and the pointed distal end 230. The means of heating and connection means need not be restricted to the use of a wire. However, any suitable means of heating and connection means known in the art may be used.

The cauterising portion 225 is between the distal end 230 of the instrument 200 and the lateral opening 220 for receiving the tissue sample. The cauterising portion 225 is in the form of a ring around the shaft 215 of the instrument 200. The cauterising portion 225 is heated by means for heating the cauterising portion 225. In this case, a wire 210 running along the length of the shaft 215 within the shaft 215 is used to connect the power supply to the cauterising portion 225. In order to ensure effective cauterisation of the tissue, it would be advantageous to concentrate the heat at the cauterising portion 225. Therefore, the wire 210 is covered with insulating material (not shown) to prevent heat from being dissipated to the shaft 215, particularly if the shaft 215 is made of conducting material.

Figure 9B:
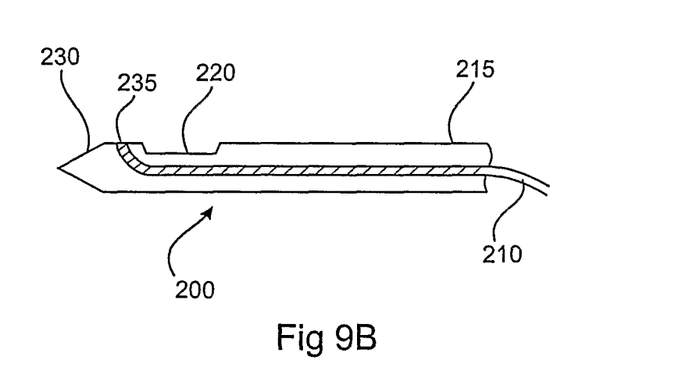

According to a further aspect of the present invention, and with reference to FIG. 9B, the cauterising portion 235 of the instrument 200 may be a part of a ring around the shaft 215. The cauterising portion 235 is found between the distal end 230 of the instrument 200 and the lateral opening 220 of the shaft 215. The cauterising portion 235 is connected to the power supply (not shown) by means of a wire 210 running along the length of the hollow shaft 215. As described above, the wire 210 is covered by insulating material (not shown) to prevent the heat supplied to the cauterising portion 235 from dissipating to the shaft 215, particularly if the shaft 215 is made of conductive material.

Figure 9C:
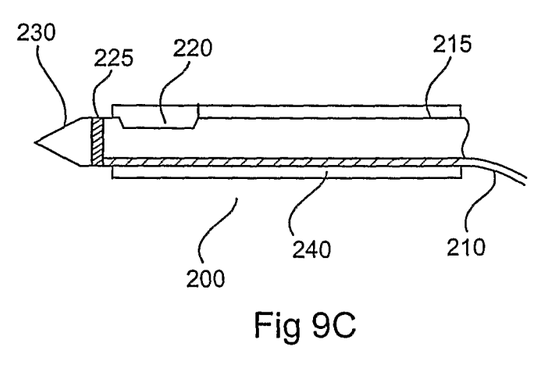

In FIG. 9C, which is similar to FIG. 9A, the instrument 200 is covered by an external insulating material 240 such that only the cauterising portion 225 and the lateral opening 220 are exposed. This would be particularly advantageous if the shaft 215 is made of conductive material, so as to prevent the heat supplied to the cauterising portion 225 from dissipating to the rest of the shaft 215 and the surrounding. It should be noted that the external insulating material 240 may be used in any instrument 200 as shown in FIG. 9A or 9B, particularly if the shaft 215 is made of conductive material.

Figure 9D:
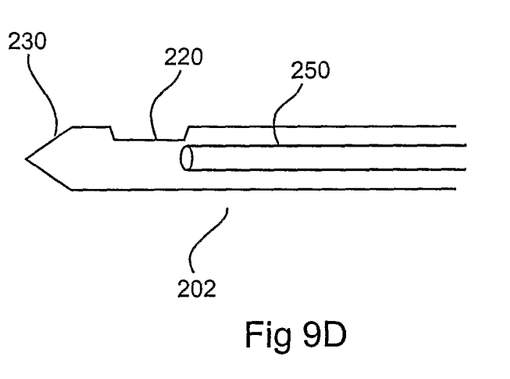

FIG. 9D shows an instrument 202 which works in a similar fashion as instrument 200 of FIG. 9A. However, the instrument 202 is such that the means for sampling comprises an inner cutter 250 that acts as the cauterising portion. When heat is supplied to this inner coaxial cutter 250, the tissue is cauterised.

Accordingly, the present invention also provides a method for the use of an instrument such as instrument 200 as shown in FIGS. 9A-C. A method of obtaining tissue samples and cauterising the remaining tissue comprising the steps of:
  introducing a biopsy and/or sampling instrument of the present invention into a tissue mass;
  severing a tissue sample from the tissue mass which has entered a lateral opening of the instrument;
  transporting the severed tissue sample to a proximal end of the instrument;
  depositing the severed tissue sample; and
  cauterising the tissue.

The tissue sample may be from any tissue. In particular, the tissue may be mammalian tissue. More in particular, the tissue may be human tissue and even more in particular, breast tissue. However, tissues such as kidney and liver tissues may also be sampled and cauterised.

The method, with reference to the instrument 200 (FIGS. 9A-C), may further comprise the step of rotating the instrument 200 such that the cauterising portion 225 (FIG. 9A or C) or 235 (FIG. 9B) of the instrument 200 is in a predetermined angular orientation. The method may further comprise the step of cauterising the tissue while sliding the instrument 200 within a tissue.

The cauterising portion 225 (FIG. 9A or C) or 235 (FIG. 9B) of the instrument 200 is heated by means of heat supplied by a power supply, to which the cauterisation portion 225 or 235 is connected. The power supply is switched on only when the cauterising portion 225 or 235 is to be used. Thus, the method also comprises the step of a user of the instrument 200 controlling the power supply so as to heat the cauterising portion 225 or 235 only when necessary, preferably after the cauterisation portion 225 or 235 is at or near the tissue mass that is to be cauterised.

The device as so described in its various embodiments may further support other peripheral uses. These may include catheter placement and marker placement. Catheter placement may be useful for the drainage of abscesses and placement of wires for ablation of tumour tissue. With respect to breast biopsies, a marker may be placed after the removal of the lesion to identify the site of the biopsy for purposes of further therapeutic surgery.

Conventionally, catheters are placed using the Seldinger technique. This involves the placement of a guidewire from a point in the skin to the area of concern under imaging guidance. Dilators of increasing diameters are then passed over the guidewire until such time that the tract is wide enough for the catheter to be introduced. The device according to any aspect of the invention may also serve to maintain the tract to facilitate the placement of a catheter, a means for further percutaneous therapy or marker where appropriate. If made of inert material, it may be left in situ in the tract itself to itself serve as a marker for a short time, perhaps while awaiting histological diagnosis. In addition, if further development allows it to be made of biodegradable material, it may be left for longer periods.

According to another aspect, a radiologically visible marker may be attached to the cauterising portion so that the user of the device will be able to locate the cauterising portion under X-ray or ultrasound when inserted into a tissue mass, and appropriately position the cauterising portion.

The invention claimed is:

1. A device for cauterizing tissue, the device comprising a C-shaped conductive cauterizing portion and means for heating the cauterizing portion, the device being mounted on a biopsy or sampling instrument such that the cauterizing portion is closer to a distal end of the biopsy or sampling instrument, wherein the device includes a sleeve having a C-shaped cross-section, the sleeve being sufficiently flexible to bend at least a portion of its length away from the instrument, while the remaining length remains mounted to the instrument, and wherein an uncompleted part of the cross-section of the sleeve forms a gap in the sleeve, and wherein at least part of the gap is closed by a resilient member.

2. The device according to claim 1, wherein the resilient member is at least an elastic band or an interwoven elastic fabric.

3. The device according to claim 1, wherein the cauterizing portion comprises a conductive material.

4. The device according to claim 3, wherein the conductive material is in the form of at least one of a layer and a wire.

5. The device according to claim 3, wherein the conductive material is further insulated by insulating material, leaving the cauterizing portion exposed.

6. The device according to claim 1, wherein the device is mounted on a shaft of the biopsy or sampling instrument.

7. The device according to claim 6, wherein the device is slidable along the shaft of the biopsy or sampling instrument.

8. The device according to claim 1, wherein the device is mounted on the biopsy or sampling instrument by frictional contact between the biopsy or sampling instrument and the device.

9. The device according to claim 1, wherein the device further comprises mounting means for holding the device on the biopsy or sampling instrument.

10. The device according to claim 9, wherein the mounting means comprises a locking mechanism between the device and the biopsy or sampling instrument, and wherein the mechanism comprises at least one of a press-fit, interference fit and spring loaded mechanism.

11. The device according to claim 9, wherein the mounting means comprises an adhesive layer for adhering the device to the biopsy or sampling instrument.

12. The device according to claim 1, wherein the device is mounted permanently onto the biopsy or sampling instrument.

13. The device according to claim 1, wherein the device is mounted releasably removable from the biopsy or sampling instrument.

14. The device according to claim 1, wherein the means for heating the cauterizing portion comprises connection means connecting the cauterizing portion to a power supply for heating the cauterizing portion.

15. The device according to claim 1, wherein the means for heating is connected to the conductive material.

* * * * *